(12) United States Patent
Chien et al.

(10) Patent No.: US 7,399,750 B2
(45) Date of Patent: *Jul. 15, 2008

(54) METHODS FOR CARDIAC GENE TRANSFER

(75) Inventors: Kenneth R. Chien, La Jolla, CA (US); Masahiko Hoshijma, San Diego, CA (US); John Ross, Jr., La Jolla, CA (US); Yasuhiro Ikeda, Yamaguchi (JP)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/954,571

(22) Filed: Sep. 11, 2001

(65) Prior Publication Data

US 2002/0032167 A1 Mar. 14, 2002

Related U.S. Application Data

(60) Provisional application No. 60/231,821, filed on Sep. 11, 2000.

(51) Int. Cl.
*A01N 43/04* (2006.01)
*A01N 63/00* (2006.01)
*C12N 5/00* (2006.01)
*C12N 15/00* (2006.01)

(52) U.S. Cl. .................. 514/44; 424/93.1; 424/93.2; 424/93.6; 435/320.1; 435/325; 435/455

(58) Field of Classification Search ............... 424/93.1, 424/93.2, 93.21, 93.6; 514/44; 435/69.1, 435/320.1, 325, 455

See application file for complete search history.

(56) References Cited

U.S. PATENT DOCUMENTS 5,652,122 A 7/1997 Frankel et al.

FOREIGN PATENT DOCUMENTS

| FR | 2753722 | 3/1998 |
|---|---|---|
| WO | WO 97/37224 | 10/1997 |
| WO | WO 99/30696 | 6/1999 |
| WO | WO 00/25804 | 5/2000 |

OTHER PUBLICATIONS

Armand et al Cardiovasc Res. 62(3):439-41. 2004.*
Janczewski et al Cardiovasc Res. 62(3):468-80, 2004.*
Juengst BMJ, 326:1410-11, 2003.*
Check Nature 422:7, 2003.*
Couzin et al, Science 307:1028, 2005.*
Rosenberg et al, Science 287:1751, 2000.*
Anderson, Nature 392:25-30, 1998.*
Touchette, Nat. Med. 2(1) 7-8, 1996.*
Chien et al Nat Med. 9(5):508-9, 2003.*
Lip et al, BMJ 320:104-107, 2000.*

Iwanaga et al, Chronic phospholamban inhibition progressive cardiac dysfunction and pathological remodeling after infarction in rats. J Clin Invest. 113(5):727-36, 2004.*

Hoshijima et al, Chronic suppression of heart-failure progression by a pseudophosphorylated mutant of phospholamban via in vivo cardiac rAAV gene delivery. Nat Med. 8(8):864-71, 2002.*

Dillmann, Wolfgang, Influences of Increased Expression of the $Ca^{2+}$ ATPase of the Sarcoplasmic Reticulum by a Transgenic Approach on Cardiac Contractility. Annals New York Academy of Sciences, pp. 43-48, 1998.

Donahue, J. Kevin et al. Ultrarapid, highly efficient viral gene transfer to the heart. Proc.Natl.Acad.Sci. USA vol. 94, 4664-4668, 1997.

He, Huaping et al. Effects of Mutant and Antisense RNA of Phospholamban on SR $Ca^{2+}$-ATPase Activity and Cardiac Myocyte Contractility. Circulation, 974-980, 1999.

He, Huaping et al. Influence of an Antisense Phospholamban Transcribed by an Adenoviral Vector on $Ca^{2+}$ ATPase in Cardiac Myocytes. Journal of Molecular and Cellular Cardiology, vol. 29, No. 6, A181, 1997.

Ikeda, Yasuhiro et al. In Vivo Gene Transfer of Deficient δ-Sarcoglycan Protein in BIO14.6 Cardiomyopathic Hamster Hearts. Circulation, 313, 2000.

Koss, Kimberly et al. Phospholamban: A Prominent Regulator of Myocardial Contractility. Circulation Research, vol. 79. No. 6, 1059-1063, 1996.

Logeart, Damien et al. Highly Efficient Adenovirus-Mediated Gene Transfer to Cardiac Myocytes after Single-Pass Coronary Delivery. Human Gene Therapy 11:1015-1022, 2000.

Logeart, Damien et al. How to Optimize In Vivo Gene Transfer to Cardiac Myocotes: Mechanical or Pharmacological Procedures? Human Gene Therapy 12:1601-1610, 2001.

Toyofuku, Toshihiko et al. Amino Acids $Glu^2$ to $Ile^{18}$ in the Cytoplasmic Domain of Pospholamban Are Essential for Functional Association with the $Ca^{2+}$-ATPase of Sarcoplasmic Reticulum. The Journal of Biological Chemistry, vol. 269, No. 4, 3088-3094, 1994.

Arber, S., et al (1997) MLP-deficient mice exhibit a diruption of cardiac cytoarchitechtural organization, dilated cardiomyopathy, and heart failure. *Cell.* 88:393-403.

Christensen, G. et al. (2000) High-Efficiency, Long-term cardiac expression of foreign genes in living mouse embryos and neonates. *Circulation.* 101:178-84.

Coral-Vazquez, R. et al. (1999) Disruption of the sarcoglycan-sarcospan complex in vascular smooth muscle: A novel mechanism for cardiomyopathy and muscular dystrophy. *Cell.* 98:465-74.

(Continued)

*Primary Examiner*—Sumesh Kaushal
(74) *Attorney, Agent, or Firm*—DLA Piper US LLP

(57) ABSTRACT

Methods for the delivery of genes to improve cardiac function including the use of viral vectors, isolation of the heart from systemic circulation, and induction of hypothermia/cardiac arrest are described. The method results in high-level, long-term expression of reporter genes and enhanced cardiac function in hamster models of heart disease.

18 Claims, 3 Drawing Sheets

OTHER PUBLICATIONS

French, B.A. et al. (1994) Direct in vivo transfer into porine myocardium using replication-deficient adenoviral vectors. *Circulation*. 90:2414-24.

Frommes, Y. et al. (1999) Gene delivery in the myocardium by intrapericardial injection. *Gene Ther*. 6:683-8.

Greelish, J.P. et al. (1999) Stable restoration of the sarcoglycam complex in dystrophic muscle perfused wih histamine and recombinant adeno-associated viral vector.*Nat. med*. 5:439-43.

Gutzman, R.J. et al. (1993) Efficient gene transfer into myocardium by direct injection of adenovirus vectors. *Cric. Res*. 73:1202-7.

Hajjar, R.J. et al. (1998) Modulation of ventricular function through gene transfer *in vivo*. *Proc. Natl. Acad. Sci., USA*. 95:5251-5256.

Holt, K.M. et al. (1998) Functional rescue of the sarcoglycam complex in BIO 14.6 hamster using delta-sarcoglycan gene transfer. *Mol. Cell*. 1:841-8.

Johnson, L.G. (1992) Efficiency of gene transfer for restoration of normal airway epithelial function in cystic fibrosis. *Nat. Genet*. 2:21-5.

Kaplitt, M.G. et al. (1996) Long-term gene transfer in procine myocardium aftercoronary infusion of an adeno-associated virus vector. *Ann. Thorac. Surg*. 62:1669-76.

Maeda, Y., et al. (1998) Efficient gene transfer into cardiac myocytes using adeno-associated virus (AAV) vectors. *J. Mol. Cell. Cardiol*. 30:1341-8.

Maurice. J., et al. (1999) Enhancement of cardiac function after adenoviral-mediated *in vivo* intracoronary beta-2 adrenergic receptor gene delivery. *J. Clin. Invest*. 104:21-9.

Miyamoto, M.I., et al. (2000) Adenoviral gene transfer of SERCA2a improves left- ventricular function in aortic-banded rats in transition to heart failure. *Proc. Natl. Acad. Sci. USA*. 97:793-98.

Mohri, H. et al. (1969) Method of surface-induced deep hypothermia for open-heart surgery in infants. *J. Thorac. Cardiovasc. Surg*. 58:262-70.

Nigro, V., et al. (1997) Identification of the Syrian hanster cardiomyopathy gene. *Hum. Mol. Genet*. 6:601-7.

Ryoke, T., et al. (1999) Progressive cardiac dysfunction and fibrosis in the cardiomyopathic hamster and effects of growth hormone and angiotensin-converting enzyme inhibition. *Circulation*. 100:1734-43.

Sakamoto, A., et al. (1997) Both hypertrophic and dilated cardiomyopathies are caused by mutation in the same gene, delta-sarcoglycan, in hamster: An animal model of disrupted dystrophin-associated glycoprotein complex. *Proc. Natl. Sci. USA*. 94:1387-8.

Shah, A.S. et al. (2001) In vico ventricular gene delivery of a β-adrenergic receptor kinase inhibitor to the failing heart reverses cardiac dysfunction. *Circulation* 103:1311.

Svensson, E.C., et al. (1999) Efficient and stable transduction of cardiomyocytes after intramyocardial infection or intracoronary perfusion with recombinant adeno-associated virus vectors. *Circulation*. 99:201-5.

Toyofuku, E., et al. (1994) Amino acids Glu2 to Ile 18 in the cytoplasmic domain of phospholamban are essential for functional association with the $Ca^{2+}$—ATPase of the sarcoplasmic reticulum. 269:3088-94.

Xiao, X., Li, J., and Samulski, R.J. (1998) Production of high-titer recombinant adeno-associated virus vectors in the absence of helper virus. *J. Virol*. 72:2224-32.

* cited by examiner

```
MEKVQYLTRSAIRRAETIEMPQQARQKLQNLFINFCLILICLLLICIIVMLL  S16EPLB
MEKVQYLTRSAIRRASTIEMPQQARQKLQNLFINFCLILICLLLICIIVMLL  (human)
MDKVQYLTRSAIRRASTIEMPQQARQNLQNLFINFCLILICLLLICIIVMLL  (dog)
MEKVQYLTRSAIRRASTIEMPQQARQNLQNLFINFCLILICLLLICIIVMLL  (mouse)
MEKVQYLTRSAIRRASTIEMPQQARQNLQNLFINFCLILICLLLICIIVMLL  (rabbit)
```
FIG. 1A
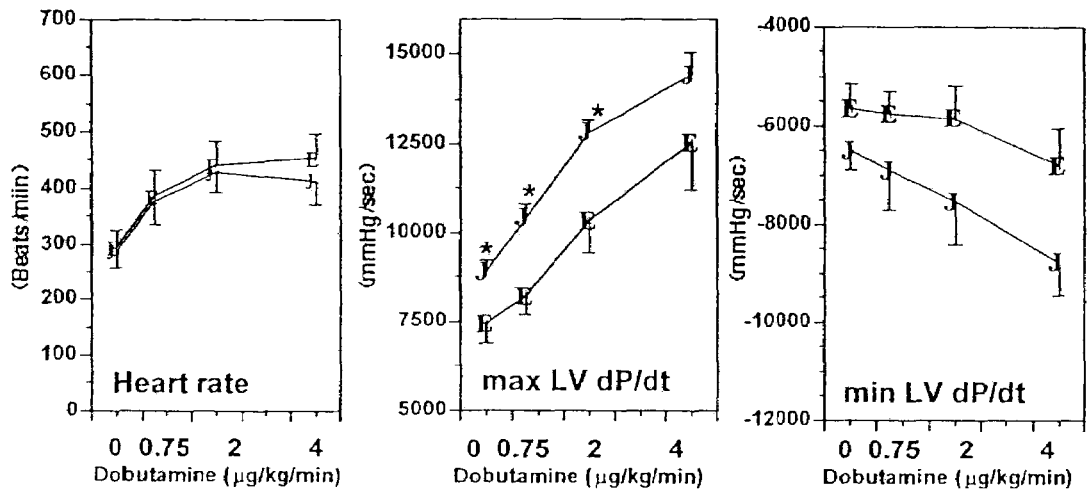
FIG. 1B
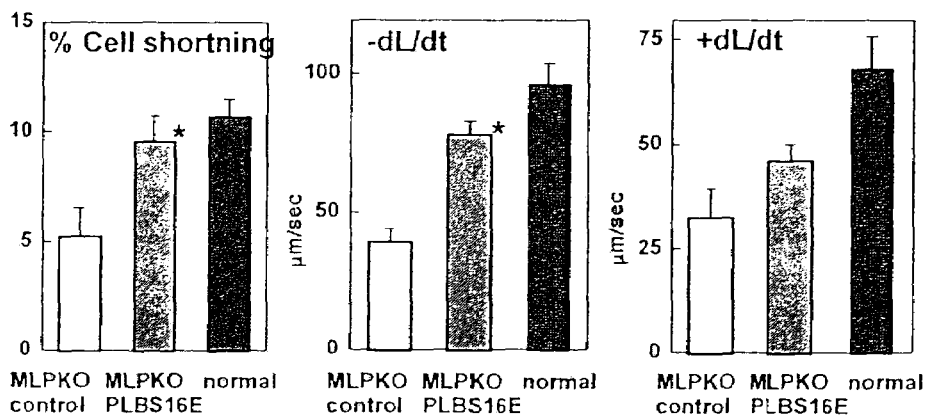
FIG. 1C

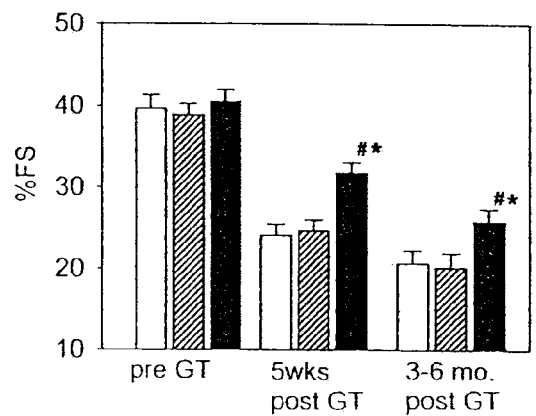
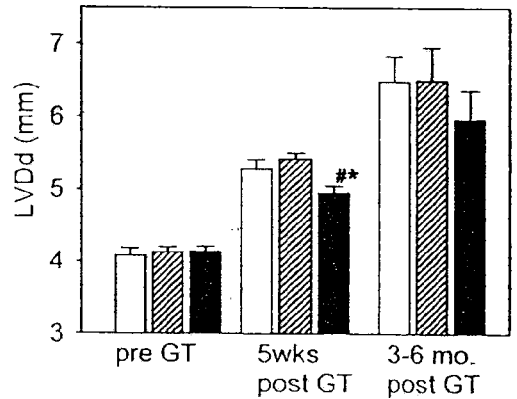
FIG. 2A　　　　　　　　FIG. 2B
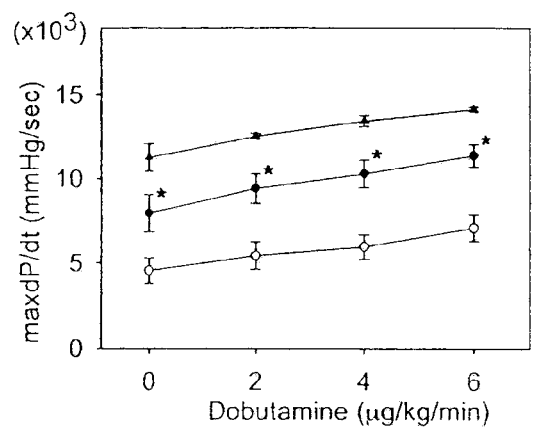
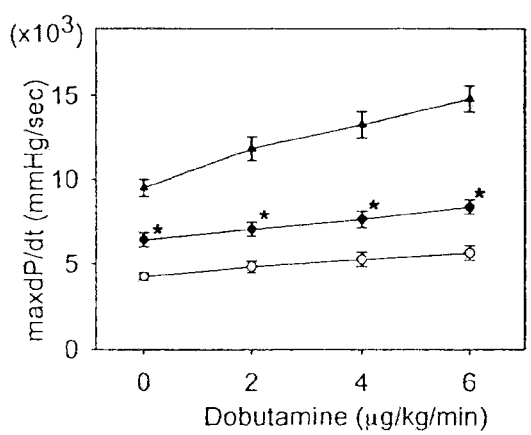
FIG. 2C　　　　　　　　FIG. 2D

METHODS FOR CARDIAC GENE TRANSFER

CROSS-REFERENCES TO RELATED APPLICATIONS

This application claims the benefit of priority of U.S. provisional application Ser. No. 60/231,821 filed Sep. 11, 2000, which is incorporated herein by reference in its entirety.

GOVERNMENT INTEREST

The invention was made with government support from the National Institutes of Health.

BACKGROUND OF THE INVENTION

Somatic gene transfer offers a myriad of possibilities for therapeutic usage in a number of diseases including congenital defects, as well as acquired forms of pathological abnormalities. There have been several critical limitations that have hindered the practical application of gene transfer in vivo. These include the duration of expression of transferred genes, the trade-off between tissue specificity and the efficiency of gene expression, and the adverse side effects of local inflammation provoked by vectors.

In the field of cardiovascular medicine, gene therapy has been focused on vascular gene transfer, mainly aimed at ischemic coronary disease. Many research groups have attempted cardiac gene transfer using adenovirus (Ad) vectors with strong, non-tissue specific gene expression cassettes driven by cytomegalovirus (CMV) or Rous sarcoma virus (RSV) promoters. Clinical trials of several angiogenic factors including vascular endothelial cell growth factor (VEGF), fibroblast growth factor (FGF) and hepatocyte growth factor (HGF) have been ongoing. The expectation is that transduction of cardiac cells with viral vectors will result in the secretion of these growth factors from cardiac cells, inducing the growth of new blood vessels and improving the blood supply to the heart to decrease ischemia.

A few publications have reported some success in the modification of cardiac function through gene transfer experimentation in rats and rabbits using intra-aorta or intra-coronary injection of virus. However, in these reports, either the extent or the specificity of gene transfer was not described properly, or the gene expression was patchy in distribution. Ascending aortic constriction was created in rats to stimulate compensatory hypertrophy which frequently results in heart failure (Miyamoto et al., 2000). Activity of the sarcoplasmic reticulum $Ca^{2+}$ ATPase (SERCA2a) is reduced in failing hearts, resulting in abnormal $Ca^{2+}$ handling, and eventually leading to contractile failure. Intracardiac injection of an Ad-SERCA2a viral vector in rats was sufficient to induce some physiological improvement; however, there were a number of limitations. Ad vectors induced robust immunological response, resulting in myocardial necrosis. Such a robust immune response would prevent the re-administration of the Ad and may result in the clearance of the transduced cells by the immune system. Although the majority of the myocytes were claimed to express the transferred gene, there was no discussion in the report regarding the transduction of other cell types in the heart, or the tissue specificity of gene expression. In a similar study by the same investigators using normal rats, patchy expression of a reporter construct in the heart was reported. Additionally expression of the transferred gene in remote organs, including lung and liver was observed (Hajjar et al., 1998).

Other attempts to improve cardiac function have focused on the β2 adrenergic receptor (β-AR). Function of β-AR is decreased in heart failure and overexpression of β-AR in otherwise normal transgenic mice results in increased cardiac function. To determine if β-AR could increase cardiac function in normal rabbits, adenovirus expressing β-AR (Ad-β-AR) was injected into the left ventricle via catheter with the aorta cross clamped for 40 seconds (Maurice et al. 1999). The delivery method produced diffuse, multichamber myocardial expression, and cardiac function was improved; however, neither the efficiency nor the specificity of gene transfer was discussed in the report. Subsequently, β-adrenergic kinase inhibitor was delivered in the post myocardial infarction hearts of rabbits via an adenovirus vector to attenuate β-AR desensitization to achieve only regional improvement of cardiac contractility (Shah et al., 2001). Thus, the demonstration of the therapeutic effect of cardiac somatic gene transfer has been hampered by the lack of in vivo gene delivery strategies to effect long-term, high-efficiency, cardiotropic expression in the intact heart.

Dysfunction of one protein may be corrected by modulation of a regulatory factor of the protein. In a study by Minamisawa et al. (1999), it was demonstrated that deletion or disruption of phospholamban (PLB), a protein that inhibits the function of SERCA2, was able to rescue cardiac defects in a mouse in which the muscle-specific LIM protein (MLP) was deleted(Arber et al., 1997). A double-knock out (DKO) mouse was generated by crossing a PLB knockout mouse with a MLP knockout mouse. The resulting mice showed few of the defects of the MLP knockout mouse strain. In this regard, genetic complementation studies in a gene targeted mouse model of dilated cardiomyopathy have identified a pivotal role for defects in sarcoplasmic reticulum calcium cycling in heart failure progression (Chien, 1999).

Dominant negative mutants of a protein may be used to inhibit function of the protein, resulting essentially in a knock out mutation. A number of dominant negative mutants of PLB have been identified and characterized by various methods (WO 00/25804 incorporated herein by reference). These mutations include the point mutations E2A, K3E, R14E, S16N, S16E, L37A, I40A and V49A as well as the double mutation K3E/R14E, some of which have only been tested in vitro (Toyofuku et al, 1994). Neonatal injection into the ventricular cavity of an Ad viral vector expressing a dominant negative form of PLB (S16 E or V49A) inhibited function of the native PLB rescuing cardiac function. High efficiency long-term in vivo cardiotropic gene transfer in several forms of chronic heart failure model had been considered a critical test to evaluate the therapeutic value of functional modification of phospholamban.

It is known from studies on cystic fibrosis that transduction of all cells is not required for improved function. Expression of the wild type sodium channel in as few as 6-10% of cells within an epithelial sheet lacking a functional sodium channel is sufficient for normal sodium ion transport (Johnson et al, 1992). This is known as the bystander effect. It is likely that sporadic expression of a calcium channel or receptor may be sufficient to increase function of a diseased tissue; however, replacement of a structural protein would likely require more efficient gene transfer. To date, there are no reports of stable, high efficiency transfer of genes into cardiac tissue.

The naturally occurring autosomal recessive Syrain hamster cardiomyopathy (CM) in BIO14.6, UMX7.1 and TO-2 hamster strains have been identified recently as being due to a mutation in the δ-sarcoglycan gene (Nigro, et al. 1997; Sakamoto, et al., 1997). This mutation results in decreased stable expression of all of the sarcoglycan genes (α, β, and γ), resulting in decreased structural integrity in all muscle cells.

The progressive left ventricular dilation, systolic and diastolic dysfunction, and cell loss in the CM hamster resemble many phenotypic features of human primary dilated cardiomyopathy (DCM) (Ryoke et al., 1999; Ikeda et al., 2000). In the hamster, these phenotypic changes are associated with increased myocardial cell permeability and rupture. In transgenic mice, disruption of the δ-sarcoglycan gene caused myocardial damage, reported to be associated at least partially with vascular smooth muscle abnormality (Coral-Vasquez et al., 1999). In transgenic mice, disruption of the δ-sarcoglycan gene has been reported to be associated with vascular smooth muscle abnormality and secondary myocardial damage (Coral-Vazquez, et al., 1999). The fragility of cells is believed to be due to the incorrect assembly of the dystrophin-associated glycoprotein complex (DAGC) (Sakamoto, et al., 1997). Normally the components of the DAGC exist perpendicular to the plane of the sarcolemma and bind to the extracellular matrix protein lanminin and the intracellular protein dystrophin, stabilizing the cell. In the absence of δ-sarcoglycan, the complex collapses and is no longer able to stabilize the cells, making them more susceptible to mechanical stress.

Rescue of skeletal muscle dystrophy of the CM hamster has been accomplished by intramuscular injection of Ad (Holt, et al., 1998) or adenovirus associated virus (AAV) (Greelish, et al., 1999) containing the δ-sarcoglycan gene. Rescue by Ad-δ-sarcoglycan was accomplished by direct injection of the Ad-δ-sarcoglycan into the quadriceps femoris. Expression was initially high ($\geq 80\%$), and some expression was seen for up to 198 days post-viral administration; however, expression decreased significantly over time. There was no discussion of expression of the gene product, or lack thereof, at remote sites.

Direct injection of AAV-δ-sarcoglycan into a small muscle (i.e. tibialis anterior) was sufficient for gene delivery throughout the muscle; however, efficient gene delivery in larger muscles (i.e. hindlimb) required delivery via circulation with concurrent disruption of endothelium using histamine. The hindlimb was isolated from systemic circulation by tourniquets, followed by injection of papaverine in histamine, and finally virus into the femoral vessel. After 4 to 6 weeks, structural integrity of cells was tested in an ex vivo system. In both systems, treatment with the δ-sarcoglycan expressing virus resulted in increased structural stability of the muscle cells. There was no discussion of gene delivery to the heart. Additionally, the isolation of the heart from circulation by tourniquet to increase exposure of the virus to the tissue of interest would clearly be problematic; therefore, the same method could not be used for cardiac tissue.

In some cases of the hereditary dystrophies, such as Duchenne's muscular dystrophy, death is usually caused by heart failure due to cardiomyopathy rather than skeletal muscle myopathy, as is the case with CM in hamsters. As the sarcoglycan gene products are structural elements of the cell, efficient transfer to nearly all cells would be required for effective treatment of the disease. Therefore methods for efficient gene transfer into cardiac muscle would be useful in the treatment of a number of muscular dystrophies.

Efficient gene delivery to the heart presents a greater problem than delivery to striated muscle tissue due to structural differences of the tissues. Striated muscle cells are large, multinucleate cells that are derived from the fusion of multiple myoblasts. Therefore, delivery of a virus particle to a single cell would result in expression over a much larger area as the RNA transcribed in a single nucleus would be transported throughout the cell. Cardiac cells contain only one or two nuclei per cell and are much smaller (10-fold). Expression in the same percentage area would require the efficient transduction of a significantly higher number of cells.

Tissue specific promoters have been used to increase specificity of myocardial gene expression, but expression levels of the transferred gene were low (Rothmann et al., 1996). Another strategy to restrict expression of transferred genes to the heart has involved direct injection of the virus into the myocardium (Gutzman et al, 1993; French et al., 1994). Another attempt involved intrapericardial virus vector injection combined with proteinase treatment (Fromes et al., 1999). These manipulations achieved local gene delivery due to a lack of intense viral vector diffusion; however, the outcome of these methods is highly restricted gene expression with local tissue damage.

The efficiency of cardiomyocyte gene delivery by an AAV vector was documented in vitro using cultured rat neonatal cells, as well as in an ex vivo system using rat papillary muscle immersion (Maeda et al., 1998). Ex vivo AAV vector transfer followed by syngeneic heart transplantation was reported to achieve high efficiency marker gene expression (Svensson et al., 1999). Transcoronary delivery of AAV was attempted in porcine myocardium; however, extremely low gene transfer efficiency was observed (0.2%) (Kaplitt et al., 1996). To date, there is no report of high efficiency in vivo cardiotropic gene delivery system with long-term sustainable expression.

Development of efficient methods for gene transfer would likely allow the correction of a number of cardiac problems.

SUMMARY OF THE INVENTION

The invention is a method for efficient gene transfer and expression in cardiac muscle cells. The invention overcomes limitations in previous methods of achieving a high level of in vivo cardiotopic gene transfer with high consistency (average 60-70% of cardiac myocytes) in normal and cardiomyopathic animal models. The invention involves increasing the dwell time of the viral vector, either Ad or AAV containing the gene of interest, in the heart by the induction of hypothermia, isolation of the heart from circulation, and near or complete cardiac arrest. Permeablizing agents are an essential component of the invention and are used during the administration of the virus to increase the uptake of the virus by the cardiac cells. The gene expression via AAV vectors is highly restricted to cardiac muscle and maintained long-term, with no signs of myocardiac inflammation.

Normal hamsters, as well as CM hamsters, were used to demonstrate the utility of the invention. Animals were anesthetized and cooled to a core temperature of about 18-25° C. on bags filled with ice water. The aorta and pulmonary artery were occluded using snares to isolate the heart from circulation. Solutions were injected into the aorta in the following sequence: modified St. Thomas' Hospital cardioplegic solution, permeablizing agents in cardioplegic solution, and finally virus, either Ad or AAV, with permeablizing agents in cardioplegic solution. The time for the isolation of the heart varied from 4 to 10 minutes before the release of the snares. The animal was resuscitated and returned to normal core body temperature.

Animals were analyzed either 4-6 days after gene transfer using Ad or 5 weeks to 3 months after gene transfer using AAV for specificity of gene transfer using reporter constructs (β-galactosidase) or for improved cardiac function using δ-sarcoglycan, dominant negative forms of PLB or other structural or functional genes. β-galactosidase expression was detected throughout the hearts of normal hamsters (78.1±30.1% with Ad and 79±8% with AAV of left ventricular myocytes per unit area expressing β-galactosidase).

Expression of δ-sarcoglycan in BIO14.6 CM hamsters deficient in δ-sarcoglycan was restored to 57.2±8.2% of that in normal golden hamsters using the Ad vector, along with marked improvement of the expression of other components of the DAGC complex. Transfer of a gene for a dominant negative form of phospholamban enhanced the contractility in the heart of CM hamsters, suppressing heart failure by enhancing the function of SERCA2. Histological analysis of the cardiac cells demonstrated that they were less damaged than cells from age matched CM hamsters.

These data demonstrate that the method of the invention is useful for the transfer of coding sequence for both structural and regulatory proteins to cardiac cells. Both Ad and AAV vectors were able to mediate efficient gene transfer and can be used equally well in the method of the invention. Choice of a viral vector would be dependent on the size of the gene to be transferred and other considerations well known to those skilled in the art. For example, a number of promoters are known to function in heart, including cytomegalovirus (CMV) and Rous sarcoma virus (RSV) promoters. These promoters may be used with or without the enhancer elements from the virus. Additionally, other elements, such as a simian virus (SV) 40 intron or other artificial intron structure may be inserted to increase gene expression. Experiments using normal hamsters without compromised cardiac function included the administration of a second dose of virus, whereas only one dose of virus was administered to BIO 14.6 hamsters to reduce the amount of time of hypothermia and isolation of the heart from circulation. The number of virus particles and the number of doses given would vary depending on the status of the patient which would be evaluated by one skilled in the art.

BRIEF DESCRIPTION OF THE DRAWINGS

The present invention will be better understood from the following detailed description of an exemplary embodiment of the invention, taken in conjunction with the accompanying drawings in which like reference numerals refer to like parts and in which:

FIG. 1 A-C Characterization of pseudophosphorylation mutant of phospholamban (S16EPLB) (A) The cross-species alignment of 52 amino-acid peptide of PLB, which is highly conserved. The phosphorylation site at Ser16 catalyzed by cAMP dependent kinase was mutated as Glu16 (SEQ ID NO:1, SEQ ID NO:2, SEQ ID NO:3, SEQ ID NO:4, and SEQ ID NO:5). (B) The catecholamine-independent upregulation of cardiac hemodynamics in S16EPLB transgenic mice. S16EPLB was placed behind 5.5 kilobase mouse α-MHC promoter (a gift from Dr. Jeffery Robbins, University of Cincinnati) and transgenic mice were generated in CB6F1 background by intra-nuclear injection. Heart rate (left), maximum (middle) and minimum (right) first derivatives of LV pressure change with increased doses of dobutamine, the β-adrenergic agonist, were measured in control animals (open circles, n=8) and α-MHC-S16EPLB animals (closed circles, n=8) as described previously (Palakodeti et al, 1997). mean±SE, *$P<0.05$ (repeated measure of ANOVA, followed by post hoc Student-Newman-Keuls test). (C) Rescue of cardiomyopathic dysfunction of MLPKO ventricular cells by AdenoS16EPLB gene transfer. AdenoS16EPLB was co-injected with AdenoEGFP in day 0-3 MLPKO mouse neonates. Four-6 weeks later, the single cell contractions of transgene positive cells (S16E) and negative cells (control) from MLPKO mice and transgene positive cells from wild type mice injected with AdenoEGFP alone (normal) were measured (Christensen et al., 2000).

FIGS. 2A-D. The therapeutic effect of rAAV/S16EPLB on the progression of LV dysfunction in BIO14.6 CM hamsters. (A, B) Echocardiographic measurement of % FS (A) and LVDd (B) before, 5 weeks and 3-6 months after intra-coronary gene transfer (GT) of no virus treatment (open bar, n=10 for 5 weeks and n=16 for 3-6 months), rAAV/LacZ (hatched bar, n=11 for 5 weeks and n=11 for 3-6 months) and rAAV/S16EPLB (filled bar, n=11 for 5 weeks and n=13 for 3-6 months). mean±SE, *$P<0.05$ vs. LacZ, #$P<0.05$ vs. no virus (repeated measure of ANOVA, followed by post hoc Student-Newman-Keuls test). (C, D) Left ventricular contractility (max LV dP/dt) was assessed at baseline and in response to the increased doses of dobutamine at 5 weeks (C) and 3 months (D) after the transfection of rAAV/S16EPLB (closed circles, n=6 for 5 weeks and n=9 for 3 months), rAAV/LacZ delivery (open circles, n=7 for 5 weeks and n=5 for 3 months) and normal control F1B hamster (closed triangles, n=7 for 5 weeks and n=6 for 3 months). mean±SE, *$P<0.05$ S16EPLB vs. LacZ (repeated measure of ANOVA, followed by post hoc Student-Newman-Keuls test). The methods for cardiac functional analysis of CM hamsters by echocardiography and cardiac catheterization were reported previously (Ryoke et al, 1999).

DETAILED DESCRIPTION AND PREFERRED EMBODIMENTS

Figure 3:
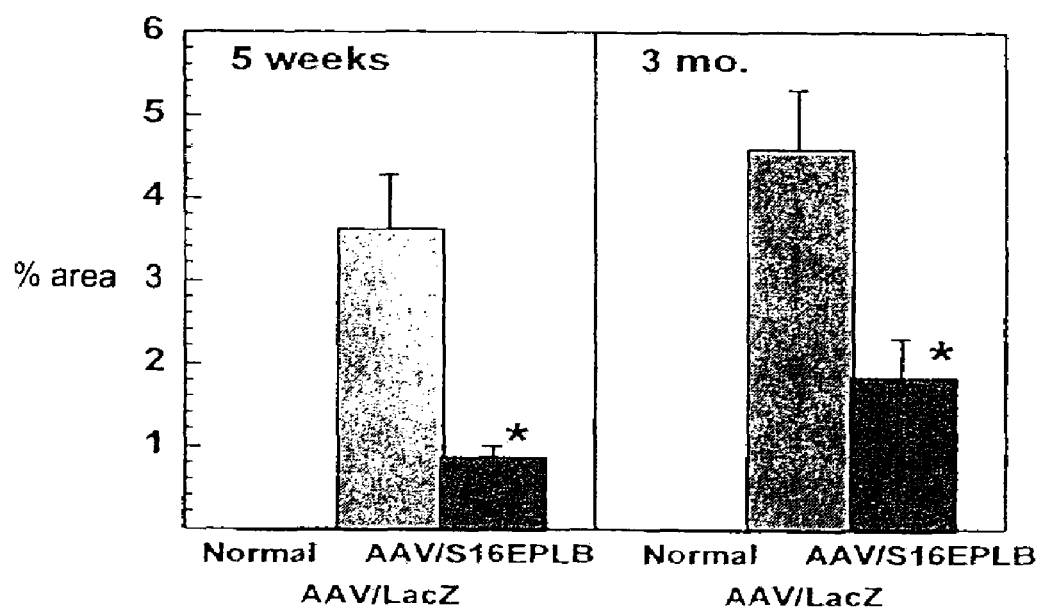
FIG. 3 Rescue of progressive myocardium cell injury with interstitial fibrosis and membrane disruption in CM hamsters by intracoronary delivery of rAAV/S16EPLB. The injured area was quantified in the sections double stained for wheat germ agglutinin and dystrophin followed by the use of NIH image software. The sections (6 transmural sections from each animal, 3 animals for each group) were from isolated LVs of 5 weeks and 3 months post gene delivery animals for rAAV/LacZ and rAAV/S16EPLB. 5 weeks old normal hamsters (F1B strain) were subjected to the same cell injury analysis. mean±SE, *$P<0.05$ S16EPLB vs. LacZ (repeated measure of ANOVA, followed by post hoc Student-Newman-Keuls test).

Cardiac gene transfer efficiency in the isolated heart is known to be affected by multiple parameters including coronary flow, dwell time, virus concentration, temperature, presence of red blood cells in the coronary perfusate, and vascular permeability. To optimize several of these factors, particularly perfusion, dwell time and vascular permeability, total body hypothermia together with cardiac arrest was induced and permeablizing agents such as histamine, substance P and serotonin were included during injection of the viral particles. This method consistently resulted in high expression of the transgene in normal and diseased hamster heart, and restored the sarcoglycan complex in BIO14.6 CM hamster hearts.

The hypothermic technique is based on that used for human neonatal cardiovascular surgery performed in the 1960's, which allowed for cardiac arrest for up to 1 hour (Mohri et al., 1969). Also, total body hypothermia in dogs with cardiac arrest for at least 45 minutes was safely accomplished (Mohri et al., 1968). This method allows for a large increase in the dwell time of the virus in the heart, increasing the transduction efficiency. Permeablizing agents also increased the efficiency of transduction. Ad injections without vascular permeablizing agents resulted in limited transgene expression. Histamine contributed to achieving complete cardiac arrest, presumably by improving myocardial perfusion. However, its main effect was undoubtably to increase vascular permeability. The short term increase in vascular permeability produced by histamine has been shown to result from endothelial gap fenestration, an effect that allows virus particles to enter the extravascular space.

Gene transfer of δ-sarcoglycan strikingly increased the protein expression of the other sarcoglycan proteins present in the DAGC, suggesting that the δ-sarcoglycan gene expresses a protein that is properly folded and targeted to its proper location in the cell. This demonstrates that a transfer of a gene coding for a structural protein into cardiac cells is feasible and can result in substantial correction of a mutant sarcolemmal protein deficiency may carry implications for the future treatment of some forms of genetic human DCM.

The high efficiency gene transfer method was applied to rescue the impairment of excitation-contraction (E-C) coupling and associated defects in cardiac contractile performance observed in CM hamsters. Ablation of PLB, rescued a spectrum of phenotypes found in a mouse model of dilated cardiomyopathy in which the mouse harbors a deficiency in cytoskeletal protein MLP (Minamisawa et al., 1999). A dominant negative interfering mutant of PLB was designed and inserted into a AAV vector to determine if disruption of PLB activity could also rescue a deficiency in the δ-sarcoglycan gene in the CM hamster. The dominant negative PLB contained a glutamic acid in the place of a serine at amino acid 16 (S16EPLB), thus the PLB could no longer be phosphorylated by a cyclic-AMP dependent protein kinase. An rAAV-LacZ vector was used as a control. The two AAVs were transferred to the myocardium of 5-6 week old BIO14.6 hamsters by the method above, in which mild stage of heart failure had been confirmed by echocardiography. Five weeks and 3-6 months after gene delivery, echocardiography and high fidelity left ventricular (LV) pressure measurement were performed to evaluate in vivo cardiac function. Treatment with AAV-S16EPLB gene transfer suppressed the progressive impairment of cardiac contractility in these animals, demonstrating the efficacy of the gene transfer method to functionally modify the cardiac pump performance.

EXAMPLE 1

Construction of viral vectors. A replication deficient (E1A and E1B deleted) Ad vector was constructed that contains the β-galactosidase gene with a nuclear localization signal sequence (Ad.CMV LacZ) or the hamster δ-sarcoglycan gene (Ad.CMV δ-sarcoglycan) driven by the CMV promoter. The viral constructs were generated by the use of the shuttle vector PACCMV.PLPA by the method of Graham et al., 1995 (incorporated herein by reference). Ad vectors generated by in vitro recombination were amplified in 293 cells. Cells were harvested and subjected to three freeze-thaw cycles to release the virus particles. Virus was purified through two consecutive CsCl gradients. The average titers of the viruses were $1.27 \times 10^{11}$ pfu/ml for AdV.CMV LacZ and $5.5 \times 10^9$ pfu/ml for Ad.CMV δ-sarcoglycan.

AAV vectors are based on the non-pathogenic and defective parvovirus type 2 and were constructed essentially as described by Xiao, et al. 1998 (incorporated herein by reference). Briefly, the three plasmid constructs, a shuttle vector, a packaging vector and a non-infectious mini-adenovirus helper vector were cotransfected into 293 cells to generate replication deficient virus particles. AAV viral particles were recovered from two sequential CsCI gradients or a single-step heparin column method. The average titer of the viruses was $1-3 \times 10^{12}$ viral particle (VP)/ml for both AAV-LacZ and AAV-S16EPLB.

EXAMPLE 2

In vivo transduction. Hamsters were anesthetized with sodium pentobarbitol (85 mg/kg, i.p.), intubated and ventilated, ECG electrodes were placed on the limbs and a 6F thermistor catheter was inserted into the rectum. The chest was shaved and a small (4-5 mm) left anterior thoracotomy performed in the second intercostal space; braided silk ligature were looped around the ascending aorta and the main pulmonary artery and threaded through plastic occluder tubes. Through a midline neck incision, the right carotid was exposed, cannulated with flame-stretched PE-60 tubing and the tip advanced into the ascending aorta just above the aortic valve (below the aortic snare) for measurement of arterial pressure and later injections of viral particles.

Bags filled with ice water were placed around the supine animal, including the head, and the heart rate and temperature were monitored every three minutes until the core temperature reached 18° C. (average time 40 minutes in the normal hamster). The aorta and pulmonary artery were then occluded and the solutions injected into the aorta in the following sequence: modified St. Thomas' Hospital cardioplegic solution (20 mM KCl, 2 µl/g body weight (BW)), 10 seconds later, 20 mM histamine (2.5 µl/g BW) dissolved in cardioplegic solution; 5 minutes later, virus solution (100 µl) with histamine and cardioplegic solution; 2 minutes later, a second injection of virus with histamime was performed in normal hamsters. Due to decreased baseline function in the CM hamsters, only one viral injection was made. Both snares were released (approximately 10 minute occlusion period for normal hamsters, 6 minute occlusion period for CM hamsters) and intra-aortic infusion of dobutamine (10 µg/kg/min) was started with periodic chest compression. Recovery of sinus rhythm and arterial pressure usually occurred in 1-2 minutes after starting dobutamine. When systolic arterial pressure reached about 50 mm Hg, the animal was placed on a heating pad (42° C.) and warmed gradually to 36° C. The chest was then closed and, intrathoracic air evacuated by suction, the animals allowed to recover.

In later experiments, it was shown that mild hypothermia (24-26° C.) and shorter aortic occlusion time (4-5 min) resulted in only mild loss of transfection efficiency (67.5%, not significant from the 77.3% efficiencies using the initial protocol).

EXAMPLE 3

Transduction procedure using a reporter gene does not alter cardiac function. Normal hamsters (n=10) were studied by echocardiography (ECG) at 4 days post Ad.CMV LacZ administration. The percent fractional shortening (% FS) of the left ventricle was 43.88±5.45%, indicative of normal function and the left ventricle end-diastolic dimension (LVDd) was 4.38±0.22 mm, indicative of normal heart size. In a group of age-matched normal, untreated hamsters, the % FS was 46.83±2.43 and the LVDd was 4.12±0.3 mm (not significantly different). In the CM hamsters, some animals were examined by echocardiography both pre- and 6 days post-administration of Ad.CMV LacZ. The left ventricular function was depressed in control CM hamsters vs. wild-type hamsters as expected (% FS 27.77±3.17%, LVDd 5.44±0.25 mm) and somewhat further depressed 6 days later (% FS 23.59±4.93%, LVDd 5.60±0.37 mm, both p<0.05).

EXAMPLE 4

Expression of β-galactosidase and δ-sarcoglycan in BIO14.6 hamsters using an Ad vector. In the CM hamster hearts transduced with Ad.CMV LacZ, there was a similar gene transfer efficiency to that in normal hamsters. A tendency for positive staining of the left ventricle to be greater than that of the right ventricle was observed, and the transduction was somewhat less homogeneous than in normal hearts. In the Ad.CMV δ-sarcoglycan transduced hearts, the δ-sarcoglycan protein expression averaged 57.2±8.2% of that in the normal heart as determined by western blot. Increases in α- and β-sarcoglycan were even larger than the increase seen in δ-sarcoglycan. In both non-transduced and the LacZ transduced CM hearts, δ-sarcoglycan expression was not detected and α- and β-sarcoglycan protein expression was very low. Thus, there was a successful restoration of the sarcoglycan complex in the BIO14.6 hamster hearts.

In other experiments, at 1 and 3 weeks after Ad.CMV δ-sarcoglycan gene transfer, clear and diffuse restoration of δ-sarcoglycan (and other sarcoglycans) to the sarcolemma and t-tubules was demonstrated by immunostaining.

EXAMPLE 5

Expression of β-galactosidase in hamsters using an AAV vector. $1 \times 10^{12}$ virus particles/kgBW AAV-LacZ were administered to normal and BIO14.6 CM hamsters by the method of the invention. Expression of LacZ analyzed 4-6 weeks and 3-6 months after administration of the virus. Homogeneous expression of LacZ was seen throughout the left ventricle with >60% of the myocytes transduced. In contrast, no significant LacZ staining was observed in other major organs including lung, liver, spleen, kidney, aorta, esophagus, testis, and skeletal muscle.

EXAMPLE 6

Expression of dominant negative phospholamban disrupts the function of the wild type protein. Phospholamban is a highly conserved 52 amino-acid peptide with two distinct phosphorylation sites: Ser16 (cyclicAMP-dependent kinase: protein kinase A) and Thr17 ($Ca^{2+}$-calmodulin dependent kinase). The in vivo inotropic and lusitropic effects of β-adrenergic agonists are mainly regulated by the phosphorylation of Ser16 of PLB by protein kinase A and the de-phosphorylation mediated primarily by the sarcoplasmic reticulum (SR) bound phosphatase type 1. Since protein kinase A phosphorylation has been shown to relieve the inhibition of SERCA2 by the dissociation of the inhibitory action of PLB, we generated a pseudophosphorylated PLB mutant by replacing Ser16 with the basic aminoacid glutamine, thereby introducing a negative charge at position 16 (S16EPLB) (FIG. 1A). To directly test the ability of S16EPLB to activate an inotropic effect in single cardiac cells, we utilized an in vivo adenoviral vector delivery protocol. Expression of the S16EPLB led to the constitutive activation of contractility and relaxation in wildtype mouse ventricular cells in the absence of catecholamines. To examine whether S16E would have a similar effect in the in vivo intact heart, we generated transgenic mice which harbor an S16EPLB gene driven by α-MHC promoter. RNA blot analysis revealed approximately a five-fold overexpression of the S16E transgene over endogenous PLB levels. These transgenic mice had no evidence of morphogenic defects, hypertrophy, or cardiomyopathy, but displayed a basal increase in cardiac contractility in the absence of catecholamine stimulation, that was qualitatively similar to the cardiac phenotype of the phospholamban null mice (FIG. 1B). Subsequently, we transferred AdenoS16EPLB in MLP deficient neonatal cardiac cells. The markedly depressed contractility and relaxation properties found in isolated MLPKO cells was partially rescued by S16EPLB at 4-6 weeks after neonatal gene transfer (FIG. 1C).

EXAMPLE 7

Enhancement of cardiac contractility by administration of a dominant negative phospholamban. To directly compare the potential therapeutic effects of the recombinant adenovirus vector versus MV mediated expression of S16E, we generated AAV-S16EPLB and AAV-LacZ vectors (Xiao et al., 1998) and examined their respective effects on the progression of heart failure in BIO14.6 CM hamsters (5-34 weeks of age). At 5-6 weeks of age, the CM hamsters have clear evidence of cardiac dysfunction, with a significant decrease in fractional shortening (% FS) assessed by echocardiography (normal hamster 47.0±6.7, n=15 vs. CM hamster 39.6±7.2, n=14, P=0.006). Within the following 28 weeks, the CM hamsters developed rapidly progressive heart failure that is comparable to NYHA (New York Heart Association) class III, characterized by echocardiography with a marked decrease in % FS (at 18 weeks old, normal hamster 44.0±4.9, n=14 vs. CM hamster 24.1±4.3, n=10, P<0.001) and chamber dilation indicated by an increase in end-diastolic left ventricular chamber dimension (LVDd) (at 18 weeks old, normal hamster 4.46±0.37, n=14 vs. CM hamster 5.28±0.41, n=10, P<0.001). Intra-coronary administration of the AdenoS16EPLB significantly enhanced cardiac contractility indicated by an approximately 33% increase in mean velocity of circumferential fiber shortening (mVcf) 6 days after transfection, while Ad-LacZ gave no significant effect. LVDd reduction also occurred in AdenoS16PLB transfected animals (6% decrease, p<0.05 vs. pre-operative measurement), whereas Ad-LacZ injected animals showed slight further enlargement in LV chamber, thereby documenting the short term efficacy of PLB inhibition.

The long-term therapeutic efficacy of the intracoronary delivery of rAAV-S16EPLB in CM hamsters was also evaluated. Echocardiography demonstrated that the rAAV/S16EPLB gene transfer strongly suppressed the progressive impairment of cardiac contraction and chamber dilation found in the CM hamsters five weeks post-gene transfer (FIGS. 2A, B). The maximum first derivatives of left ventricle (LV) pressure, LV max dP/dt was largely reversed toward the level of normal hamsters by rAAV/S16EPLB treatment at baseline as well as in response to the increased doses of the β-adrenergic agonist, dobutamine (FIG. 2C). This effect of AAV-S16EPLB to mitigate the development of heart failure was further evident at 3-6 months post-gene transfer, with a substantial improvement in % FS (AAV-S16EPLB animals, 25.9±5.7, n=13 vs. AAV-LacZ animals 20.2±6.2, n=11, P<0.05) (FIG. 3A) and mVcf (AAV-S16EPLB animals, 3.4±0.7, n=13 vs. AAV-lacZ animals 2.7±0.7, n=11, P<0.05). The high fidelity left ventricular pressure measurement directly documented that the AAV mediated delivery of the pseudophosphorylation mutant PLB sustained its rescue effect on cardiac contractility for at 3 months post-gene delivery (FIG. 2D), displaying an over 50% increase of LV max dP/dt in the S16EPLB-transferred animals compared to LacZ controls. The persistent expression of the S16E peptide was evidenced by immuno-blotting analyses with an anti-PLB and anti-phospho 16-PLB antibodies (S16EPLB peptide vs. endogenous PLB=1.5-5:1, n=6), and southern blotting suggested that CMV-S16EPLB fusion gene is at least partially integrated in the host genome, which suggests that expression may indeed by long-term. Taken together, these data provide direct evidence that PLB inhibition can lead to chronic reversal of heart failure by employing a novel AAV mediated gene therapy strategy, even at stages of the disease that correspond to severe near end-stage human heart failure (late NYHA Class III).

EXAMPLE 8

Expression of a domainant negative phospholamban decreases damage in failing cardiac cells. Previous experimental and clinical studies have documented that chronic increases in contractility mediated by β-adrenergic agonists or phosphodiesterase inhibitors can lead to the rapid progression of heart dysfunction in chronic heart failure. Furthermore, administration of β-blockers may improve survival and the progression of clinical heart failure. The mechanisms which underlie this detrimental long term effect have been ascribed to catecholamine toxicity, and have raised the query as to whether the chronic stimulation of cardiac performance by catecholamine is inherently driving heart failure progression. By utilizing a novel intracoronary AAV system to deliver a pseudophosphorylated PLB mutant which constitutively activates cardiac contractility in the absence of cAMP stimulation, the current study challenges this notion. By short circuiting the β-adrenergic system at a downstream point in the pathway that controls SR calcium cycling and cardiac contractility, we have shown that chronic increases in cardiac contractility can lead to a long-term reversal of cardiac dysfunction and a marked effect on heart failure progression. In this study, we provide evidence suggesting that one of the mechanisms for the sustained therapeutic effects of AAV-S16EPLB gene delivery in CM hamster model system relates to an effect on slowing the rate of myocyte cell death which underlies heart failure progression in this model. Histological analysis at 5 weeks post gene transfer revealed that cardiac interstitial fibrosis, which is progressive in the human cardiomyopathy was downregulated for an extended time period by AAV-S16EPLB gene delivery, and that the degree of cell injury, as assessed by the stability of the dystrophin complex, was significantly diminished in the animals treated with the rAAV/S16EPLB (FIG. 3).

Although an exemplary embodiment of the invention has been described above by way of example only, it will be understood by those skilled in the field that modifications may be made to the disclosed embodiment without departing from the scope of the invention, which is defined by the appended claims.

REFERENCES

Arber, S., et al (1997) MLP-deficient mice exhibit a diruption of cardiac cytoarchitechtural organization, dilated cardiomyopathy, and heart failure. *Cell.* 88:393-403.

Christensen, G. et al. (2000) High-efficiency, long-term cardiac expression of foreign genes in living mouse embryos and neonates. *Circulation.* 101:178-84.

Coral-Vazquez, R. et al. (1999) Disruption of the sarcoglycansarcospan complex in vascular smooth muscle: A novel mechanism for cardiomyopathy and muscular dystrophy. *Cell.* 98:465-74.

French, B. A. et al. (1994) Direct in vivo transfer into porine myocardium using replication-deficient adenoviral vectors. *Circulation.* 90:2414-24.

Frommes, Y. et al. (1999) Gene delivery in the myocardium by intrapericardial injection. *Gene Ther.* 6:683-8.

Graham, F. L. and Prevec, L. (1995) Methods for construction of adenovirus vectors. *Mol. Biotechnol.* 3:207-20.

Greelish, J. P. et al. (1999) Stable restoration of the sarcoglycam complex in dystrophic muscle perfused with histamine and recombinant adeno-associated viral vector. *Nat Med.* 5:439-43.

Gutzman, R. J. et al. (1993) Efficient gene transfer into myocardium by direct injection of adenovirus vectors. *Cric. Res.* 73: 1202-7.

Hajjar, R. J. et al. (1998) Modulation of ventricular function through gene transfer in vivo. *Proc. Natl. Acad. Sci., USA.* 95:5251-5256.

Holt, K. M. et al. (1998) Functional rescue of the sarcoglycam complex in BIO 14.6 hamster using delta-sarcoglycan gene transfer. *Mol. Cell.* 1:841-8.

Ikeda, Y., et al. (2000) Altered membrane proteins and permeability correlate with cardiac dysfunction in cardiomyopathic hamsters. *Am J Physiol Heart Circ Physiol.* 278: H1362-70.

Johnson, L. G. (1992) Efficiency of gene transfer for restoration of normal airway epithelial function in cystic fibrosis. *Nat. Genet* 2:21-5.

Kaplitt, M. G. et al. (1996) Long-term gene transfer in porcine myocardium after coronary infusion of an adeno-associated virus vector. *Ann. Thorac. Surg.* 62:1669-76.

Maeda, Y., et al. (1998) Efficient gene transfer into cardiac myocytes using adeno-associated virus (AAV) vectors. *J. Mol. Cell. Cardiol.* 30:1341-8.

Maurice, J., et al. (1999) Enhancement of cardiac function after adenoviral-mediated in vivo intracoronary beta-2 adrenergic receptor gene delivery. *J. Clin. Invest.* 104:21-9.

Miyamoto, M. I., et al. (2000) Adenoviral gene transfer of SERCA2a improves left-ventricular function in aortic-banded rats in transition to heart failure. *Proc. Natl. Acad. Sci. USA.* 97:793-98.

Mohri, H. et al. (1968) Challenge of prolonged suspended animation. A method of surface-induced deep hypothermia. *Ann. Surg.* 168:779-87.

Mohri, H. et al. (1969) Method of surface-induced deep hypothermia for open-heart surgery in infants. *J. Cardiovasc. Surg.* 58:262-70.

Nigro, V., et al. (1997) Identification of the Syrian hamster cardiomyopathy gene. *Hum. Mol. Genet.* 6:601-7.

Rothman, T, et al. (1996) Heart muscle-specific gene expression using replication defective recombinant adenovirus. *Gene Ther.* 3:919-26.

Ryoke, T., et al. (1999) Progressive cardiac dysfunction and fibrosis in the cardiomyopathic hamster and effects of growth hormone and angiotensin-converting enzyme inhibition. *Circulation.* 100:1734-43.

Sakamoto, A., et al. (1997) Both hypertrophic and dilated cardiomyopathies are caused by mutation in the same gene, delta-sarcoglycan, in hamster: An animal model of disrupted dystrophin-associated glycoprotein complex. *Proc. Natl. Acad. Sci. USA.* 94:13873-8.

Shah, A. S. et al. (2001) In vivo ventricular gene delivery of a β-adrenergic receptor kinase inhibitor to the failing heart reverses cardiac dysfunction. *Circulation* 103:1311.

Svensson, E. C., et al. (1999) Efficient and stable transduction of cardiomyocytes after intramyocardial infection or intracoronary perfusion with recombinant adeno-associated virus vectors. *Circulation.* 99:201-5.

Toyofuku, E., et al. (1994) Amino acids Glu2 to Ile 18 in the cytoplasmic domain of phospholamban are essential for functional association with the $Ca^{2+}$-ATPase of the sarcoplasmic reticulum. 269:3088-94.

Xiao, X., Li, J., and Samulski, R. J. (1998) Production of high-titer recombinant adeno-associated virus vectors in the absence of helper virus. *J. Virol.* 72:2224-32.

We claim:

1. A method for treating heart failure associated with loss of cardiac muscle contractility in a patient, comprising directly administering to cardiac muscle a viral gene expression vector encoding a phospholamban (PLB) gene having an S16E mutation therein, which improves SERCA2 medicated cardiac muscle contractility.

2. The method of claim 1, wherein the viral gene expression vector further comprises a promoter suitable for use in cardiac muscle.

3. The method of claim 1, wherein the viral gene expression vector is an adeno-associated viral vector (AAV).

4. The method of claim 1, further comprising co-administering a viral gene expression vector encoding a sarcoplasmic reticulum CA2+ ATPase (SERCA-2) gene with the viral gene expression vector encoding the PLB gene to the cardiac muscle.

5. The method of claim 1, wherein the phospholamban gene further enhances SERCA-2 activity in the cardiac muscle.

6. The method of claim 1, wherein the phospholamban gene is administered with a permeabilizing agent.

7. The method of claim 6, wherein the permeabilizing agent is histamine, substance P or serotonin.

8. The method of claim 1, wherein the patient is a human.

9. The method of claim 1, wherein the patient is suffering from cardiac arrest or brachycardia with heart failure at the time that the gene is administered.

10. The method of claim 1, wherein the heart is isolated from systemic circulation at the time that the gene is administered.

11. The method of claim 1, wherein practice of the method reduces the occurrence of cardiac interstitial fibrosis.

12. The method of claim 1, wherein the viral expression vector is an adenoviral vector.

13. A method for treating heart failure associated with loss of cardiac muscle contractility in a patient, comprising administering to cardiac muscle by intracoronary injection a viral gene expression vector encoding a phospholamban (PLB) gene having an S16E mutation therein, which improves SERCA2 medicated cardiac muscle contractility.

14. The method of claim 13, wherein the viral gene expression vector further comprises a promoter suitable for use in cardiac muscle.

15. The method of claim 13, wherein the viral gene expression vector is an adeno-associated viral vector (AAV).

16. The method of claim 13, further comprising co-administering a viral gene expression vector encoding a sarcoplasmic reticulum CA2+ ATPase (SERCA-2) gene with the viral gene expression vector encoding the PLB gene to the cardiac muscle.

17. The method of claim 13, wherein the phospholamban gene further enhances SERCA-2 activity in the cardiac muscle.

18. The method of claim 13, wherein the phospholamban gene is administered with a permeabilizing agent.

* * * * *

SEQUENCE LISTING

<160> NUMBER OF SEQ ID NOS: 5

<210> SEQ ID NO 1
<211> LENGTH: 52
<212> TYPE: PRT
<213> ORGANISM: Artificial
<220> FEATURE:
<223> OTHER INFORMATION: Mutant form of humam protein sequence

<400> SEQUENCE: 1

Met Glu Lys Val Gln Tyr Leu Thr Arg Ser Ala Ile Arg Arg Ala Glu
1               5                   10                  15

Thr Ile Glu Met Pro Gln Gln Ala Arg Gln Lys Leu Gln Asn Leu Phe
            20                  25                  30

Ile Asn Phe Cys Leu Ile Leu Ile Cys Leu Leu Ile Cys Ile Ile
        35                  40                  45

Val Met Leu Leu
    50

<210> SEQ ID NO 2
<211> LENGTH: 52
<212> TYPE: PRT
<213> ORGANISM: Homo sapiens

<400> SEQUENCE: 2

Met Glu Lys Val Gln Tyr Leu Thr Arg Ser Ala Ile Arg Arg Ala Ser
1               5                   10                  15

Thr Ile Glu Met Pro Gln Gln Ala Arg Gln Lys Leu Gln Asn Leu Phe
            20                  25                  30

Ile Asn Phe Cys Leu Ile Leu Ile Cys Leu Leu Ile Cys Ile Ile
        35                  40                  45

Val Met Leu Leu
    50

<210> SEQ ID NO 3
<211> LENGTH: 52
<212> TYPE: PRT
<213> ORGANISM: Canis familiaris

<400> SEQUENCE: 3

Met Asp Lys Val Gln Tyr Leu Thr Arg Ser Ala Ile Arg Arg Ala Ser
1               5                   10                  15

Thr Ile Glu Met Pro Gln Gln Ala Arg Gln Asn Leu Gln Asn Leu Phe
            20                  25                  30

Ile Asn Phe Cys Leu Ile Leu Ile Cys Leu Leu Ile Cys Ile Ile
        35                  40                  45

Val Met Leu Leu
    50

<210> SEQ ID NO 4
<211> LENGTH: 52
<212> TYPE: PRT
<213> ORGANISM: Mus musculus

<400> SEQUENCE: 4

Met Glu Lys Val Gln Tyr Leu Thr Arg Ser Ala Ile Arg Arg Ala Ser
1               5                   10                  15

Thr Ile Glu Met Pro Gln Gln Ala Arg Gln Asn Leu Gln Asn Leu Phe
            20                  25                  30

```
Ile Asn Phe Cys Leu Ile Leu Ile Cys Leu Leu Leu Ile Cys Ile Ile
        35                  40                  45

Val Met Leu Leu
    50

<210> SEQ ID NO 5
<211> LENGTH: 52
<212> TYPE: PRT
<213> ORGANISM: Oryctolagus cuniculus

<400> SEQUENCE: 5

Met Glu Lys Val Gln Tyr Leu Thr Arg Ser Ala Ile Arg Arg Ala Ser
1               5                   10                  15

Thr Ile Glu Met Pro Gln Gln Ala Arg Gln Asn Leu Gln Asn Leu Phe
            20                  25                  30

Ile Asn Phe Cys Leu Ile Leu Ile Cys Leu Leu Leu Ile Cys Ile Ile
        35                  40                  45

Val Met Leu Leu
    50
```